(12) United States Patent
Morgan, Jr.

(10) Patent No.: US 6,315,748 B1
(45) Date of Patent: Nov. 13, 2001

(54) METHOD AN APPARATUS FOR TREATMENT OF COMPRESSIVE SYNDROME CONDITIONS

(76) Inventor: Clyde E. Morgan, Jr., 20124 W. 151st St., Olathe, KS (US) 66061

( * ) Notice: Subject to any disclaimer, the term of this patent is extended or adjusted under 35 U.S.C. 154(b) by 0 days.

(21) Appl. No.: 09/663,496

(22) Filed: Sep. 18, 2000

(51) Int. Cl.[7] ....................................... A61F 5/00
(52) U.S. Cl. ........................... 602/21; 128/878; 128/879; 2/20
(58) Field of Search ..................... 128/846, 878, 128/879, 889; 602/20, 21; 2/16, 20

(56) References Cited

U.S. PATENT DOCUMENTS 5,921,949   7/1999   Dray .

OTHER PUBLICATIONS

Magister Corporation, Chattanooga, TN brochure re Rep Band (1998).
Sports Medical Rehab brochure re Resist–A–Band.
3M Product Clinical Data Sumary re No. 1521 3M Plastic Medical Tape.
Kessler et al; Friction Massage, Physical Therapy Principles and Methods, 3rd ed. 1996, Chapter 7.
Hygenic Corporation brochure re Hytone Latex Sheeting Specifications.
3M Product Specification for Plastic Medical Tape, No. 1527–L.

Primary Examiner—Michael A. Brown
(74) Attorney, Agent, or Firm—Hovey, Williams, Timmons & Collins

(57) ABSTRACT

An orthopedic device (10) is provided for the treatment of physical disorders characterized by region(s) of localized, undue compression of body tissue leading to nerve compression and/or damage, such as carpal tunnel syndrome. A carpal tunnel syndrome treatment device (10) in accordance with the invention includes a central, resilient, stretchable tensioning segment (12) with a plurality of relatively less stretchable adhesive straps (14–18) secured to the segment (12). In use, the segment (12) is placed on the back of a patient's hand (20), whereupon the straps (14–18) are pulled and adhered to the patient's palm in a fashion to expand the segment (12). In this orientation, the control segment (12) exerts continuous yielding or tensile forces through the straps (14–18) which in turn reduces carpal tunnel syndrome nerve compression and alleviates symptoms.

12 Claims, 2 Drawing Sheets

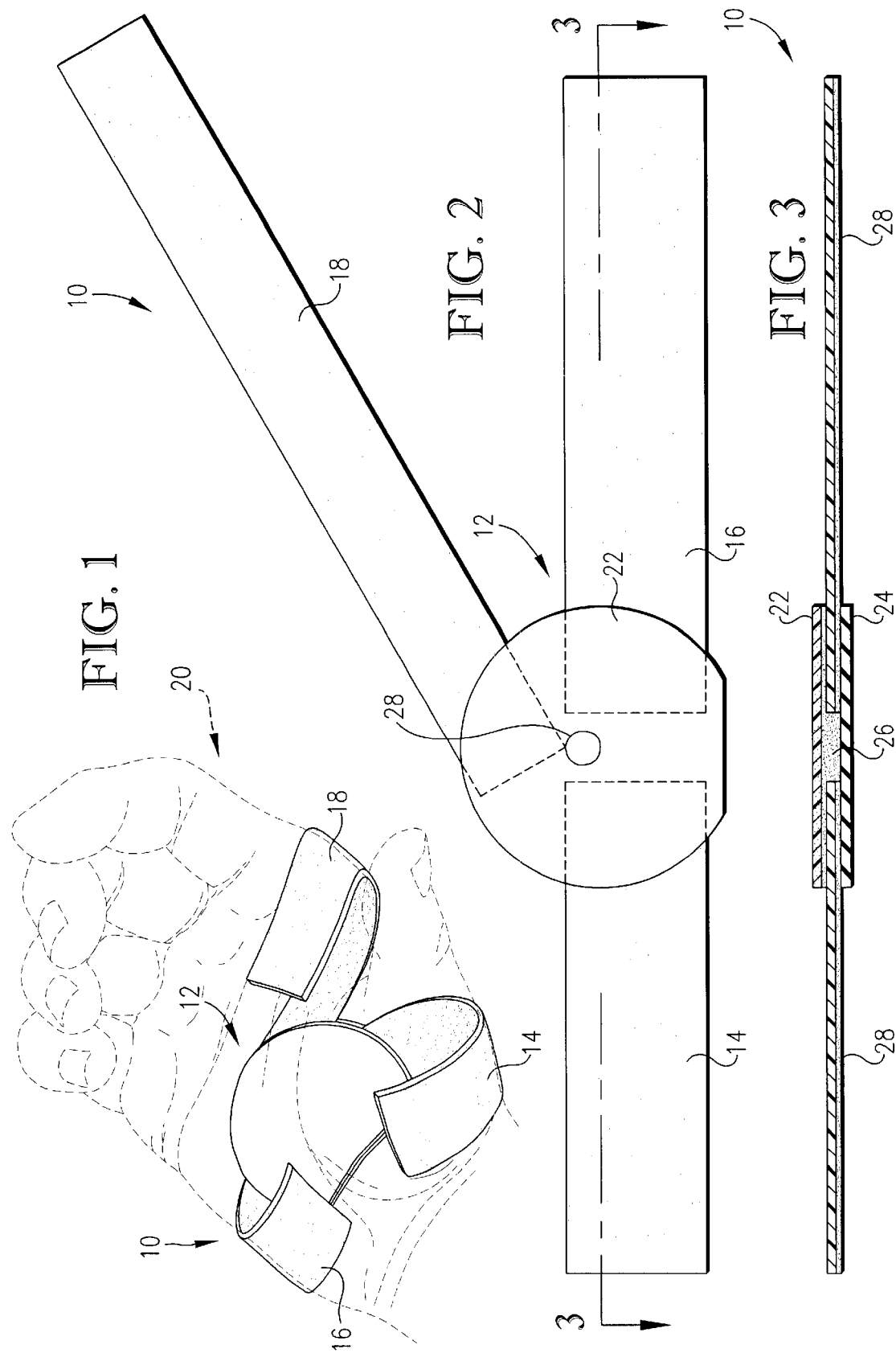

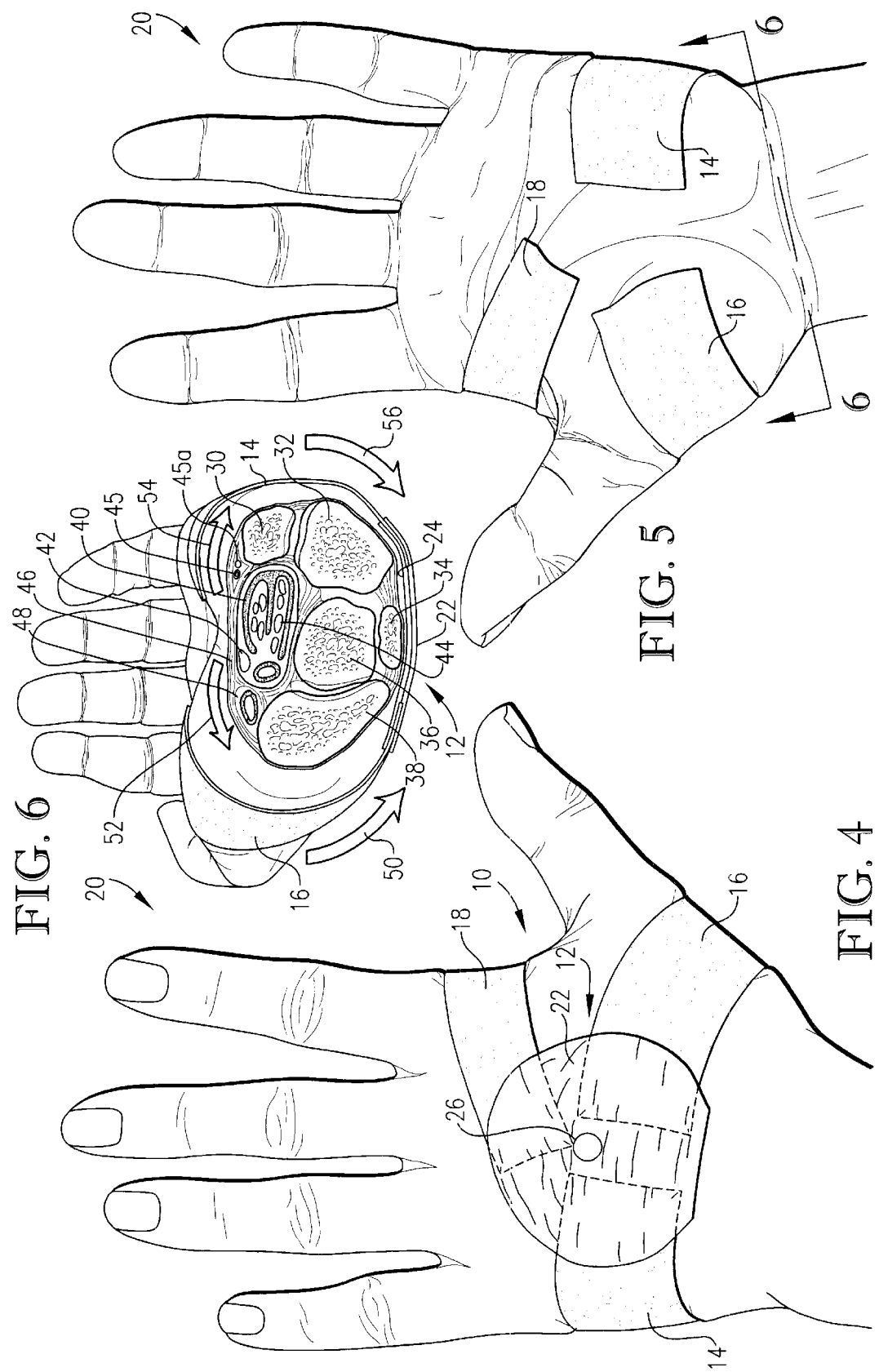

METHOD AN APPARATUS FOR TREATMENT OF COMPRESSIVE SYNDROME CONDITIONS

BACKGROUND OF THE INVENTION

1. Field of the Invention

The present invention is broadly concerned with improved method and apparatus for the treatment of compressive syndrome physical disorders characterized by a region of localized, undue compression of body tissue, for example, carpal tunnel syndrome. More particularly, the invention is concerned with such methods and devices wherein use is made of a central tensioning segment formed of resilient, stretchable material (e.g., synthetic elastomer or latex rubber) together with a plurality of adhesive attachment straps of limited stretchability secured to the tensioning segment for securement of the device on a person's body. The tensioning segment exerts a continuous yielding or tensile force through the straps, serving to at least partially reduce the troublesome tissue compression.

2. Description of the Prior Art

Carpal tunnel syndrome and related conditions result from repeated trauma to the tendons and soft tissue structures forming a part of the wrist. Excessive pressure on the carpal tunnel contents, including the flexor tendons, nerves and bursa, results in abnormal function, weakness, inflammation, pain, numbness and ultimately in nerve tissue injury.

The flexor retinaculum is a thick, relatively unyielding ligamentous band that crosses the groove on the palmer surface of the carpal bones. It is composed of the palmer (volar) carpal ligament and transverse (anterior annular) carpal ligament. The palmer carpal ligament is attached medially and laterally to the styloid processes of the radius and ulna. The transverse carpal ligament is attached medially to the pisiform bone and the hamulus of the hamate, and laterally to the tuberosity of the scaphoid and palmer surface of the ridge of the greater multangular (trapezium). The fibers of these ligaments merge at the distal end of palmer and proximal end of the transverse ligament. Together with the carpal bones and articulations, they form a tunnel through which pass the deep flexor tendons and median nerve.

The median nerve passes through the carpal tunnel adjacent the flexor retinaculum and between it and the flexor tendons and their bursa. The carpal tunnel is barely adequate to accommodate these structures and it is generally felt that any narrowing of the diameter of the tunnel or decrease in the diameter to contents ratio, causes injury to the median nerve by repeatedly pressing it against the relatively unyieldable retinaculum. Repetitive and/or constant forceful movement, in particular extension movements of the hand, are thought to repeatedly traumatize the median nerve in this manner, as does the repetitive and/or constant force contracture of the thenar muscles.

Current medical treatment of carpal tunnel syndrome consists of rest, restriction from traumatizing activities, limiting movement with restrictive splints, anti-inflammatory medication and cortisone injections. In advanced cases surgery is used to transect and spread the transverse carpal ligament to allow more room for the contents of the carpal tunnel, i.e., an increase in the diameter to contents ratio. Some form of wrist support or splint is normally used in the early stages of treatment. They are used in an attempt to delay progression of the condition or as an adjunct to some other treatment in an effort to lessen the pain and aid in the return to normal function. Subsequent to surgery, wrist splints are frequently used to support the wrist and aid in recovery. Thus it is important that a presurgical device be provided which corrects the condition or prevents further development and/or progression of the condition.

Given the widespread incidence of carpal tunnel syndrome and similar disorders, many attempts have been made to provide orthopedic supports or braces for the wrists which will alleviate the symptoms and/or provide a means of eliminating the problem in its entirety. For example, U.S. Pat. No. 5,921,949 describes a corrective support designed specifically for the treatment of a tunnel syndrome. However, none of these past efforts have resulted in a truly effective device or treatment for the syndrome. Therefore, the traditional treatments described previously remain the methods of choice in most cases.

In addition to carpal tunnel syndrome, a number of other compressive syndrome conditions have been identified. These include radial tunnel syndrome (sometimes referred to as "tennis elbow"). In this condition, the supinator muscle, while turning the wrist in the clockwise direction compresses the radial nerve. The radial nerve feeds the muscles of the back of the forearm. It is most commonly seen with twisting activities of the arm. Pain if first noticed at the lateral side of the elbow, about two inches toward the wrist from the elbow. Rest is currently the best treatment to allow swelling to go down. DeQuervain's Tenosynovitis is a problem of the abductor pollicis longus and extensor policis longus tendons which irritate the bursa coating, called tenosynovius becoming tenosynovitis when inflammation occurs. Irritation continues forming scar tissues. The present treatment protocol attempts to reduce the swelling in the area by reducing the usage.

Frozen shoulder is a joint dysfunction and is often caused by adherence of the anterinferior aspect of the joint capsule to the humeral head. This condition often occurs after injury, being a scar formation type dysfunction. Piriformis Syndrome is a condition where the sciatic nerve is compressed between the piriformis muscle and the gemellus muscle.

Guyons' Canal syndrome is a common nerve compression affecting the ulnar nerve and possibly the ulnar artery as it passes through a tunnel in the wrists on the lateral portion. The problem is similar to carpal tunnel syndrome, but involves a completely different nerve. Sometimes both conditions can be causing problems in the same hand.

Thoracic Kyphosis is the loss of movement in the upper back area, described as a derangement syndrome and is caused by adaptive shortening, as a result from poor postural habits over a sustained period. Derangement syndrome is believed to be caused by a disturbance of some structure with the joint causing mechanical deformation of pain sensitive structures.

Trigger points are muscle conditions where an involved area is relatively spasm, building up lactic acid in the muscle, with resultant pain.

After surgery, scar tissue can ball up and contract, in unnatural orientations. This can cause severe pain to a patient.

While all of these types of compressive syndrome conditions have been recognized for many years, there has been no readily available, non-surgical treatment available to alleviate the symptoms thereof.

SUMMARY OF THE INVENTION

The present invention overcomes the problems outlined above and provides an improved device for the treatment of compressive syndrome disorders such as carpal tunnel syndrome, but also including radial tunnel syndrome, DeQuervain's Tenosynovitis, frozen shoulder, Piriformis Syndrome, Guyon's Canal Syndrome, thoracic kyphosis, and scar tissue conditions. Broadly speaking, the devices of the invention include a tensioning segment formed of elastic, stretchable material adapted for placement on a persons body proximal to the region of localized tissue compression, together with a plurality of elongated, adhesives straps secured at respective locations to the tensioning segment; the straps have less stretchability (and are preferably essentially non-stretchable) than the tensioning segment and are configured for securing the tensioning segment in place on a person's body. When applied, the tensioning segment of the device exerts yielding or tensile forces through the straps serving to at least partially reduce tissue compression.

In the case of a carpal tunnel syndrome treatment device, the tensioning segment is adapted to overlie the back of a person's hand, and has three individuals straps secured thereto. Two of the attachment straps are oriented to extend end opposite directions from the tensioning segment and to wrap about the heel of the person's hand below the person's thumb; the other of the straps is oriented to wrap about the person's hand between the thumb and forefinger.

In preferred forms, the tensioning segment includes an expansion indicator allowing the user to determine the extent of expansion of the segment upon application of the device. In practice, a circular marking on the tensioning segment is used for this purpose. Additionally, the tensioning segment is preferably formed at least in part of stretchable latex material, whereas the attachment straps are made of essentially nonstretchable polyethylene film coated with pressure are sensitive adhesive.

BRIEF DESCRIPTION OF THE DRAWINGS

FIG. 1 is a perspective view all of a person's right hand (shown in phantom) with a preferred treatment device in accordance with the invention applied to the person's hand for the treatment of carpal tunnel syndrome;

FIG. 2 is a plan view of the preferred carpal tunnel syndrome treating device in accordance with the invention, with a left hand model being shown;

FIG. 3 is a sectional view taken long line 2—2 of FIG. 2 and illustrating one form of interconnection between the central tensioning segment of the device and the adhesive attachment straps;

FIG. 4 is an elevational view of the preferred treatment device of the invention, shown mounted on a person's left hand;

FIG. 5 is a view similar to that of FIG. 4, but showing the palm side of the person's left hand and the placement of the adhesive straps; and FIG. 6 is a sectional view along line 6—6 of FIG. 5 and illustrating the manner in which the treatment device alleviates the symptoms of carpal tunnel syndrome.

DETAILED DESCRIPTION OF THE PREFERRED EMBODIMENT

Turning now to the drawings, and particularly FIGS. 2 and 3, a carpal tunnel syndrome treating device 10 is illustrated. Broadly speaking, the device 10 includes a central resilient tensioning segment 12 as well as three elongated straps 14, 16 and 18 secured to be segment 12. The device 10 is designed to be applied to the hand 20 of a person in order to alleviate carpal tunnel syndrome symptoms.

In more detail, the tensioning segment 12 is made up of a pair of the arcuate, face-to-face oriented flexible sheets 22 and 24, which are bonded together by adhesive 26 or direct thermal bonding of the sheets. As illustrated, the inboard ends of the straps 14–18 are received and bonded between the sheets 22, 24, with the adhesive 26 serving to secure the straps in place; again, if the sheets 22, 24 are thermally bonded, the straps 14–18 would be secured thereto by virtue of such thermal bonding. An important feature of the invention resides in the fact that the segment 12 is formed of elastic, stretchable material which, when stretched, exerts a continuous yielding or tensile force on the straps 14–18. To this end, it is preferred that the bottom sheet 24 is formed of conventional synthetic elastomer material, whereas the upper sheet 22 is formed of adhesive-bearing medical tape which is also stretchable with the sheet 24 (in this embodiment, the adhesive forming a part of the medical tape functions as the adhesive 26; in other cases a separately applied adhesive can be employed). It will also be seen that the upper sheet 22 has an expansion indicator 28 thereon, in the form of a circular marking. Where the tensioning segment 12 is formed of heat-bonded sheets, both such sheets may be formed of appropriate synthetic resin material such as Hysynal commercialized by Hygenic Corporation. The Hysynal product has a 300% modulus (ASTM D412) of 250 psi; a tensile strength (AS TM D412) of 2200 psi; an ultimate elongation ASTM D412) of 600%; and a durometer hardness (ASTM D2240) of 40±5 Shore A (plied). A typical latex rubber used for the fabrication of the segment 12 is the Hytone latex commercialized by Hygenic Corporation. This product has a 300% modulus of 130 psi, a tensile strength of 4000 psi, and an ultimate elongation of 780%.

Generally speaking, stretchable products used in this context should have a modulus of from about 75–400 psi, a tensile strength from about 1500–5000 psi, and an ultimate elongation of from about 200–1000% (ASTM D412).

Each of the straps 14–18 have significantly less stretchability than the tensioning segment 12. Preferably, these straps are formed of essentially non-stretchable medical quality tape or ethylene vinyl acetate, with a layer 28 of conventional skin adhesive on the underside thereof. This adhesive is advantageously hypoallergenic in order to eliminate skin irritation. As seen, the opposed straps 14 end 16 have a width somewhat greater than that of the angularly oriented strap 18.

It will be appreciated that the device 10 will be provided in left and right hand versions. The right hand version is illustrated in FIG. 1, whereas the left hand version is shown in FIGS. 2–5.

The device 10 is applied to the hand 20 of a person in the general manner shown in FIGS. 1 and 4–5. That is, in the first step, the tensioning segment 12 is placed on the back of the person's hand. Next, the straps 14 and 16 are sequentially pulled and applied to the palm region of the hand 20 as best seen in FIG. 5. During this application of the straps 14, 16, the user observes the indicator 26, and pulls the second-applied strap sufficiently to enlarge the indicator by approximately 30%. In the final step, the strap 18 is pulled upwardly and angularly between the thumb and forefinger of the hand, with the outer end of the strap being applied to the palm region of the hand 20 above the ends of the straps 14, 16, insuring that the outboard ends of the straps 14–18 do not overlap in the palmar region. Here again, during application of the strap 18, the indicator circle 26 is used so as to insure a substantially even expansion of the tensioning segment 12.

In more detail, during the first week of using the device 10, the tensioning segment 12 is placed on the back side of the hand, between the first bend of the small finger and where the wrist bends, with the straight edge of the segment 12 at the center of the hand. Next, the strap 14 is applied as described previously, followed by the straps 16 and 18. During the first week, the device 12 is worn for period of 10–16 hours per day. During the second week of therapy, the segment 12 is placed on the back side of the hand, just distal to where the wrist bends on the side of the little finger, with the edge of the segment at the center of the hand. Placement of the straps 14–18 is the same as during the first week. After the second week, further use of the device 10 is carried out to achieve the most comfort and pain relief for the patient.

Attention is next directed to FIG. 6, which depicts the manner in which it is believed that the device 10 operates to alleviate the symptoms of carpal tunnel syndrome. As illustrated, the human wrist includes a complex of articulations and tendons including the Pisiform, Triquetral, Lunate, Capitate, and Scaphoid bones 30–38, respectively, the common synovial sheath 40, median nerve 42, digit tendons 44, ulnar artery 45, ulnar nerve 45a, and flexor retinaculum 46. The carpal tunnel 48, through which the median nerve 42 passes, is also illustrated in FIG. 6. As explained previously, carpal tunnel syndrome involves a condition wherein the median nerve 42 and surrounding tissues are subjected to undue compression, which is accompanied by shortening of the flexor rentinaculum.

Use of the device 10 alleviates carpal tunnel syndrome symptoms by virtue of the continuing yielding or tensile forces exerted on the straps 14–18 by the tensioning segment 12. That is, and as indicated by directional arrows 50–56, the segment 12 effectively "pulls" at the area of the carpal tunnel and flexor rentinaculum to lengthen the latter, thereby enlarging the carpal tunnel 48 and relieving pressure on the median nerve 42 and ulnar nerve 45a.

The device 10 is also advantageous in that it can be worn by a patient without interfering with the patient's normal activities; indeed, the device can be worn while sleeping or during daytime routines, even under gloves or other protective equipment. At the same time, the invention reduces the possible need for carpal tunnel syndrome surgery and obviates tiresome repetitive exercises and other related physical therapies.

Although a device for treating carpal tunnel syndrome has been specifically illustrated and described herein, it will be appreciated that the invention is not so limited. First and foremost, devices may be provided having as few as two straps and as many as needed for a particular condition. Thus, for the treatment of tennis elbow, it is anticipated that only a two-strap model would be required, with the central tensioning segment applied adjacent the proximal radial head of the radial bone, and with the two-straps extending in opposite directions therefrom. By exerting tension against the stronger muscle in this region, and providing more support for the adjacent weaker muscle, the tendency for the tissue to remain in an abnormal position is lessened, by reducing the intrinsic concentric muscular contraction.

Similarly, scar tissue conditions can be alleviated using devices in accordance with the invention. In such therapy, two of the devices would typically be used, one on each side of the scar formation. In this fashion, a stress is exerted in a direction parallel with the normal fiber orientation so as to stimulate reorientation of the involved scar tissue.

Patients suffering from trigger point muscle conditions can also be helped using the devices hereof. Two approaches can be used in this context. First, the device can be placed with one of the strap ends over the trigger point pain area, with the other strap end over a normal muscle. During motion, the applied device tends to extend the contracted trigger point muscle. Alternately, a plurality of individual devices may be placed about the trigger point muscle area to generate muscle extension forces.

I claim:

1. A device for treating physical disorders characterized by a region of localized, undue compression of body tissue, said device comprising:

a tensioning segment formed of elastic, stretchable material adapted for placement on a person's body proximal to said region; and a plurality of elongated, adhesive straps secured at respective locations to said tensioning segment, said straps having less stretchability than said tensioning segment and being configured for securing said tensioning segment in place on the person's body, said tensioning segment exerting forces through said straps serving to at least partially reduce said compression at said region.

2. The device of claim 1, said device adapted for the treatment of carpal tunnel syndrome, said tensioning segment adapted to overlie the back of a person's hand, there being three of said straps secured to said tensioning segment, two of said segments oriented to extend in the opposite directions from said segment to wrap about the heel of the person's hand below the person's thumb, the other of said straps wrapping about the person's hand between the person's thumb and forefinger.

3. The device of claim 1, said tensioning segment including an expansion indicator permitting the user to determine the extent of expansion of the tensioning segment in different directions, upon attachment of the device.

4. The device of claim 3, said expansion indicator comprising a circular marking on the outer face of said tensioning segment.

5. The device of claim 1, said tensioning segment including a pair of opposed, flexible sheets adhesively secured together.

6. The device of claim 5, the ends of said straps being received and sandwiched between said flexible sheets.

7. The device of claim 1, each of said straps formed of polyethylene film having one face thereof coated with a pressure sensitive acrylate adhesive.

8. The device of claim 1, said tensioning segment formed of resilient latex.

9. The device of claim 1, said device being configured for the treatment of conditions selected from the group consisting of radial tunnel syndrome, DeQuervain's Tenosynovitis, frozen shoulder, Piriformis Syndrome, Guyon's Canal Syndrome, thoracic kyphosis, and scar tissue conditions.

10. A method of treating a physical disorder characterized by a region of localized, undue compression of body tissue, said method comprising the steps of:

placing a tensioning segment on a person's body proximal to said region, said tensioning segment formed of elastic, stretchable material and having a plurality of elongated, adhesive straps secured to the tensioning segment at respective locations of thereon, said straps having less stretchability than said tensioning segment; and stretching said tensioning segment by exerting tensile forces through said straps, and adhesively attaching said straps on the person's body, said tensioning segment exerting forces through said straps serving to at least partially reduce said compression at said region.

11. The method of claim 10, said physical disorder being carpal tunnel syndrome, said placing step comprising the step of placing said tensioning segment on the back of the person's hand, said stretching and attaching step comprising the steps of extending a pair of said straps in opposite directions from said segment and wrapping the straps about the heel of the person's hand below to person's thumb, and extending a third straps from said tensioning segment and wrapping the third straps about the person's hand between the person's thumb and forefinger.

12. The method of claim 10, said disorder selected from the group consisting of radial tunnel syndrome, DeQuervain's Tenosynovitis, frozen shoulder, Piriformis Syndrome, Guyon's Canal Syndrome, thoracic kyphosis, and scar tissue conditions.

* * * * *